United States Patent [19]
Bobier-Rival et al.

[11] Patent Number: 5,652,266
[45] Date of Patent: Jul. 29, 1997

[54] COSMETIC OR DERMATOLOGICAL COMPOSITIONS

[75] Inventors: Carinne Bobier-Rival, Cergy; Odile Fournier, Rueil Malmaison; Alain Fructus, Courbevoie, all of France

[73] Assignee: The Boots Company PLC, Nottingham, England

[21] Appl. No.: 411,346

[22] Filed: Mar. 27, 1995

[30] Foreign Application Priority Data

Apr. 1, 1994 [FR] France .................................. 94 03873

[51] Int. Cl.⁶ ........................... A61K 31/19; A61K 31/07
[52] U.S. Cl. ........................ 514/557; 514/568; 514/574; 514/725; 514/736; 514/937; 514/938
[58] Field of Search ........................... 514/532, 557, 514/568, 725, 938, 574, 736, 937

[56] References Cited

U.S. PATENT DOCUMENTS 5,153,230  10/1992  Jaffery .................................. 514/847

FOREIGN PATENT DOCUMENTS 2310767  10/1976  France .
2188233   9/1987  United Kingdom .

*Primary Examiner*—Phyllis G. Spivack
*Attorney, Agent, or Firm*—Nikaido, Marmelstein Murray & Oram LLP

[57] ABSTRACT

A cosmetic or dermatological composition containing a skin enhancing agent consisting essentially of a) at least one α-hydroxy acid, b) salicylic acid or esters thereof and c) at least one retinoid in a skin enhancing method.

7 Claims, No Drawings

COSMETIC OR DERMATOLOGICAL COMPOSITIONS

The use by dermatologists of α-hydroxy acids at doses of 30 to 70% is a very old use for reducing deep scars. For example, the use of lactic acid has been proposed for the treatment of certain skin pathologies and for the control of keratinization. The use of many types of α-hydroxy acids is known for treating hyperkeratinizations such as calluses, dandruff, cracked skin, ichthyosis, acne, very dry skin, actinic keratoses, blemishes caused by aging. For example, in U.S. Pat. No. 3,878,537, glycolic acid, citric acid, malic acid, tartronic acid, tartaric acid, glucuronic acid, pyruvic acid, 2-hydroxybutyric acid, 3-hydroxybutyric acid and lactic acid are described for treating ichthyosis. The recommended pH of the preparations is 3.5 to 7.5. The acid content varies from 1 to 20% and the composition can be a mixture of water and alcohol or a suitable ointment.

The action of the α-hydroxy acids seems to occur at the level of the deep layers of the stratum corneum. This mechanism is not completely clear but it seems that it takes place in two phases, firstly, blocking of the ionic binding sites between the corneocytes and secondly, blocking of the enzymatic systems of sulfatase and phosphorylase type (see Ichihara et al., J. Biol. Chem., Vol. 0225, pp. 945–958 (1957)).

The use of salicylic acid is well known in dermatology for its keratolytic effect. Moreover, the combination of α-hydroxy acids and salicylic acid is mentioned in Patent DD 274,357. Salicylic acid is a powerful keratolytic agent by direct action (solubilization) on the keratin of the uppermost layers of the horny layer.

The use of the retinoids is well known in dermatology and in cosmetology for treatments of acne, actinic keratoses and wrinkles caused by aging. It would seem that the retinoids destroy the desmosomes of the keratinocytes and therefore cause desquamation. Furthermore, the retinoids are recognized by receptors of the cell nucleus and act on the regulation of the differentiation of the keratinocytes by stimulating it.

The combination of Vitamin A and α-hydroxy acids is described by U.S. Pat. No. 5,153,230. Thus, the uses of α-hydroxy acids combined with salicylic acid or with vitamin A is known in the treatment of keratinization disorders. The. pH's used in these various preparations are 3.5 to 7.5, more rarely 3.0 to 6.0.

With known cosmetic compositions, the side effects such as stinging, redness or burning sensations are not inconsiderable. Once the amounts of α-hydroxy acids is greater than 20%, rinsing is necessary after a certain application time which makes these compositions virtually unsuitable for a cosmetic use and restricts them to a medically-controlled use.

OBJECTS OF THE INVENTION

It is an object of the invention to provide novel cosmetic and dermatological compositions for enhancing skin without the disadvantages of the prior art and a method of enhancing skin.

These and other objects and advantages of the invention will be obvious from the following detailed description.

THE INVENTION

The cosmetic and dermatological compositions of the invention contain a skin enhancing agent consisting essentially of a) at least one α-hydroxy acid, b) salicylic acid or esters thereof and c) at least one retinoid.

It has been surprisingly found that the use of a composition containing at least three active ingredients, amongst which are at least one α-hydroxy acid, salicylic acid or an ester thereof or a mixture of esters of this acid and at least one retinoid, allows the desquamating and moisturizing effects of the α-hydroxy acids, the keratolytic effect of salicylic acid and the desquamating effects and keratinocyte differentiation stimulating effects of the retinoids to be combined. The use on the skin of such a combination allows the treatment of problems associated with aging by a gentle desquamating effect and regeneration of the epidermis. Other uses of the invention relate to problems associated with a hyperkeratinization such as acne, actinic keratoses, blemishes caused by ageing, dry and very dry skin.

The previously described combination, by allowing different and complementary actions, does not require such high concentrations as in the case of a product on its own or in double combination, and therefore has a better tolerance on the skin.

The cosmetic or dermatological compositions according to the invention preferably contain a) 3 to 20%, preferably 4 to 15%, of at least one α-hydroxyacid, b) 0.1 to 5%, preferably 0.3 to 4%, of salicylic acid or 0.2 to 10%, preferably. 0.6 to 8%, of an ester or a mixture of esters of salicylic acid and c) 0.02 to 2%, preferably 0.04 to 1%, of retinoid. The percentages are expressed as a % of the total weight of the composition.

Examples of α-hydroxy acids are preferably lactic acid, glycolic acid, malic acid, tartronic acid, tartaric acid, glucuronic acid, pyruvic acid, 2-hydroxyisobutyric acid, 3-hydroxybutyric acid, citric acid, galacturonic acid, mandelic acid, mucic α-phenyllactic acid, α-phenylpyruvic acid, saccharic acid, α-hydroxybutyric acid, α-hydroxyisobutyric acid, α-hydroxyisocaproic acid, α-hydroxy-isovaleric acid, atrolactic acid, galactanic acid, pantoic acid, glyceric acid, isocitric acid, dihydroxymaleic acid, dihydroxytartaric acid, dihydroxy-fumaric acid and benzylformic acid. Lactic acid and glycolic acid are preferred. Preferably, the combination of the two acids is used.

In addition, esters of α-hydroxy acids can also be used which have the effect of releasing the α-hydroxy acids into the skin more slowly. Among these esters are preferably cosmacol ETL® (Di C14–C15 alkyl tartrate), cosmacol ECL® (Tri C14–C15 alkyl citrate), cosmacol ELI® (C12–C13 alkyl lactate), cosmacol FOI® (C12–C13 alkyl octanoate), cosmacol EMI® (Di C12–C13 alkyl malate), cosmacol ECI® (Tri C12–C13 alkyl citrate), cosmacol ETI® (Di C12–C13 alkyl tartrate). The doses of these esters, alone or in a mixture, vary from 2 to 15% and preferably from 4 to 10% of the total weight of the composition.

Among the preferred esters of salicylic acid which can be used on its own or in a mixture are isodecyl salicylate, tridecyl salicylate or isopropylbenzyl salicylate.

Examples of retinoids are retinol, retinol acetate, retinol palmitate, 13-cis retinoic acid, all-trans retinoic acid, retinoylphospholipids such as retinoyl 13-cis phosphatidylethanol or retinoyl all-trans phosphatidyl-ethanol.

The retinoids can be used in pure form or in solution in an oil or an alcohol. They can be in the form of liposomes or oily vesicles surrounded by a layer of phospholipids, cholesterol and fatty acids such as LIPOMICRONS® from the SEDERMA Company or NANOFUTURE® from Pr WEBER or NANO-COS® from the INDUCHEM Company. The purpose of these different forms is to protect the retinoids from oxidation and chemical degradation during manufacture of the final product and during storage of the product before use. Their purpose is also to facilitate penetration of the retinoids into the skin.

The retinoids can also be combined with liquid crystals such as the LICRITHERM® from the MERCK Company or liquid crystals from the HALLCREST Company. The purpose of these liquid crystals is also to protect the retinoids and to facilitate their penetration into the skin.

The combination described in the present invention is preferably presented in the form of an aqueous gel, a simple or multiple emulsion, but other forms are also possible. In the case of a simple emulsion, the water-in-oil emulsion will preferably be chosen. It has been found that in the choice of a water-in-oil emulsion, the pH of the aqueous solution containing the α-hydroxy acid or acids and salicylic acid or at least one of its esters, could be very low, particularly between 1.8 and 2.5, without there being harmful effects after use on the skin. This very low pH also allows the acid content to be reduced for an equivalent effectiveness.

In the case of a multiple emulsion, the water-in-oil-in-water emulsion is preferred. The mixture of the α-hydroxy acid or acids and salicylic acid or an ester or a mixture of its esters will be in the internal aqueous phase with a pH preferably between 1.8 and 2.5.

Also a subject of the invention is the treatment of actinic keratoses by adding to the previously described mixture nordihydroguaiaretic acid (or NDGA) or an ester of NDGA such as NDGA phosphatinyl ethanol (NDGA acid grafted in position 2 of a phosphatinyl ethanol) and therefore a particular subject of the invention is such compositions. The concentration of NDGA or of NDGA ester can be from 0.05 to 10% relative to the total composition, preferably from 0.1 to 5%. The cosmetic composition containing α-hydroxyl acids, salicylic acid or an ester or a mixture of its esters, a retinoid and NDGA, by its desquamating, keratolytic and regenerating effects, is particularly good at repairing skin suffering from actinic keratosis.

Also useful is the treatment of blemishes caused by aging by adding to the mixture described previously at least one agent known for its anti-blemish effects and therefore a more particular subject of the invention is such compositions. Agents known for their anti-blemish effects are for example kojic acid (0.01 to 2%), LICORICE PT® from the NIKKO Company (0.01 to 3%), calcium Panthotine sulfonate (0.1 to 5%), methiosilane C+® from the EXYMOL Company (from 1 to 10%), ARBUTINE (active ingredient of Bucerole) (from 0.1 to 5%) or its liposome form (from 1 to 10%), MELAWHITE® from the PENTAPHARM Company (from 0.5 to 5%), UNIMONTAN® from the INDUCHEM Company (from 1 to 10%), and CELL SEED EXA® from the SPCI Company (0.01 to 1%).

Also useful is the treatment of acne. In fact, the previously described combination allows, by its desquamating and keratolytic action, the unblocking of the sebaceous orifices whose excessive keratinization is the first stage in the etiology of comedones, micro-cysts, then acne pimples. One or more active substances suitable for the treatment of acne can be added to the previously-described mixture, preferably anti-bacterial agents, sebum-regulating agents, anti-inflammatories, anti-lipases, absorbents of sebum or fatty acid and astringents.

These anti-acne agents are more particularly chosen from: oleyl acetate (0.5 to 5%) anti-lipase, Hafnia biolyzate (0.01 to 1%) anti-inflammatory, (as described by FR-B 8406559) CITRICINAL® (0.01 to 1%) bactericide, chlorhexidine hibitane (0.2 to 3%) bactericide, juniper essential oil (0.01 to 2%) bactericide, sodium undecylenate (0.2 to 3%) bactericide, zinc acetate (0.2 to 2%) bactericide, trichlorocarban (0.05 to 2%) bactericide, ALCLOXA® from the HOECHST Company (0.2 to 3%) astringent, MICROPEARL® from the SEPPIC Company (1 to 10%) sebum absorbent, TAKALOPHANE® from the NIKKO Company (0.5 to 5%) fatty acid absorbent, kaolin (1 10%) sebum absorbent, stearylglycyrrhetinate (0.2 to 2%) anti-inflammatory, glycyrrhetinic acid (0.1 to 2%) anti-inflammatory, LIPACIDE PVS® from the SEPPIC Company (0.5 to 5%) anti-inflammatory, essential extract of sesame oil from the EXPANSCIENCE Company (0.2 to 5%) anti-inflammatory, peroxidized corn oil EPALINE 100® from the CARILENE Company (1 to 10%) anti-inflammatory, DEFATTED RICE BRAN PF-60® from the TSUNO Company (0.5 to 10%) sebum absorbent, SHISO extract (Jan Dekker, France) (0.2 to 3%) bactericide, SUNPHENON® (Jan Dekker, France) (0.2 to 2%) bactericide and PHILOROGINE® from the SECMA Company (0.2 to 5%) sebum regulator.

A preferred composition of the invention is a composition containing 4 to 15% by weight of lactic acid, 0.3 to 4% by weight of salicylic acid or 0.6 to 8% by weight of one of its esters and 0.04 to 1% by weight of vitamin A palmitate.

Also useful is the treatment of skin ageing by the addition to the previously-mentioned mixture of active molecules such as anti-elastase products (for example an extract of Klebsiella pneumonia), anti-radical products (for example extracts of silymarin mixed or not with tocopherol), natural or synthetic ceramides (such as ceramide 2) or ceramide equivalents (such as ceramide HO3 from the SEDERMA Company).

The process of the invention for the preparation of cosmetic and dermatological composition comprises forming a water-in-oil emulsion of the silicone type and adding to the emulsion an aqueous phase of the α-hydroxy acid, salicylic acid or its esters and at least one retinoid.

In the following examples, there are described several preferred embodiments to illustrate the invention. However, it should be understood that the invention is not intended to be limited to the specific embodiments.

EXAMPLE 1

Preparation of a skin-care cream intended to combat ageing by desquamating and regenerating action The following oily phase was prepared:

| | |
|---|---|
| Isocetyl stearate | 3 g |
| Sorbitan sesquioleate | 0.8 g |
| Hydrogenated ricin oil | 0.9 g |
| Jojoba oil | 1 g |
| PEG-45 (dodecyl glycolcopolymer) Elfacos ST 9 ® from the AKZO Company | 1 g |
| Cyclomethicone/dimethicone copolyol | 9 g |
| Volatile silicone | 4 g |

This oily phase was heated at about 60° C. until a completely homogeneous mixture was obtained.

In addition, the following aqueous phase was prepared:

| | |
|---|---|
| Water | 45.98 g |
| 40% lactic acid solution obtained by fermentation of sugar cane juice, apple and lemon juice and with | 10 g |

| | |
|---|---|
| 2% green tea extract added to it | |
| 55% glycolic acid | 1 g |
| Sodium chloride | 0.8 g |
| Tetrasodium EDTA | 0.05 g |
| Polysaccharide obtained by fermentation (sclerosium gum) | 0.6 g |
| Glycerin | 3 g |
| Propylene glycol | 3 g |
| PEG-400 | 1.5 g |
| Methylparaben | 0.25 g |
| Propylparaben | 0.15 g |
| O-cymen-5-ol | 0.1 g |

These products were mixed until dissolution was complete and the pH of the aqueous phase was adjusted to 2.3 with about 0.07 g of pure sodium hydroxide. The aqueous phase was then added with vigorous stirring to the oily phase at a temperature of 60° C. The water/silicone emulsion formed immediately and stirring was continued for about half an hour while reducing the stirring and allowing the temperature to fall to ambient temperature. Salicylic acid dissolved beforehand in ethanol was then added with reduced stirring:

| | |
|---|---|
| Salicylic acid | 0.5 g |
| 95° ethanol | 3 g |

Then, a suspension of 6 g of Lipomicron® of vitamin A palmitate (corresponding to 0.1 g of the retinoid), 0.3 g a perfume and finally 3 g of Luzenac talc were added with moderate stirring. This emulsion had a viscosity of 24,000 cP (measured with a Brookfield RVT viscometer, 24 hours after production at a temperature of about 20° C.). It was stable under centrifugation (15 min. at 5,000 rev/min.) and for more than 3 months at a temperature of 42° C. This emulsion was called Preparation I.

By operating as in Example 1, the following compositions were prepared:

EXAMPLE 2

The following water/oil emulsion was prepared:

| Oily phase: | |
|---|---|
| ABIL EM90 ® (cetyl dimethicone copolyol) | 4 g |
| Polysorbate 20 | 0.2 g |
| Jojoba oil | 1 g |
| ELF Acos ST 45 ® | 0.6 g |
| C12–15 alkylbenzoate | 5 g |
| Cosmacol ECI ® | 5 g |
| Vitamin A palmitate | 0.12 g |
| Silicone fluid | 2 g |
| Isodecyl salicylate | 1.5 g |
| Aqueous phase: | |
| Glycerin | 3 g |
| Sclerosium gum | 0.2 g |
| Sodium chloride | 0.8 g |
| Lactic acid | 5 g |
| Glycolic acid | 1 g |
| Caustic soda | S.Q. for pH 2.2 |
| Preservatives | 0.5 g |
| Perfume | 0.2 g |
| Water | S.Q. for 100 g |

EXAMPLE 3

Water/oil emulsion with another type of emulsifying agent was prepared

| Oily phase: | |
|---|---|
| Arlacel 1689 ® | 3 g |
| Caprylic/capric triglyceride | 4 g |
| Isohexadecane | 8 g |
| Vaseline oil | 5 g |
| Tridecyl salicylate | 2 g |
| Isopropyl benzyl salicylate | 2 g |
| Retinoyl 13-cis phosphatidylethanol | 0.5 g |
| Aqueous phase: | |
| Glycerin | 4 g |
| Magnesium sulfate | 0.5 g |
| Lactic acid | 4 g |
| Glycolic acid | 2 g |
| Cosmacol ECL ® | 2 g |
| Preservatives | 0.5 g |
| Perfume | 0.3 g |
| Water | S.Q. for 100 g |

EXAMPLE 4

| Oily phase: | |
|---|---|
| Jojoba oil | 5 g |
| Di-isocetyl cyclohexane | 5 g |
| Silicone fluid | 2 g |
| Retinol acetate | 1 g |
| Perfume | 0.5 g |
| Aqueous phase: | |
| SEPIGEL 305 ® | 3 g |
| Isononyl isononanoate | 5 g |
| Silicone fluid | 2 g |
| Glycolic acid | 2 g |
| Malic acid | 3 g |
| Preservatives | 0.5 g |
| 96° alcohol | 5 g |
| Salicylic acid | 0.5 g |
| Penederm PP15 ® | 2 g |
| Water | S.Q. for 100 g |

Use of the cosmetic composition

The aim of the study was to show the superiority of the composition of the invention (Preparation I) relative to the other mixtures (Preparations II, III, IV and V), on the speed of desquamation of cells of the stratum corneum by the dihydroxyacetone (DHA) method.

A) Methodology

The study was carried out on 5 healthy caucasian subjects, 4 of which were women and 1 of which was a man, from 25 to 50 years old.

Products:

5 products were tested:

| | |
|---|---|
| Preparation I | Product as described in Example 1 |
| Preparation II | Placebo, |
| Preparation III | Preparation I, but without lactic acid, |
| Preparation IV | Preparation I, but without salicylic acid, |
| Preparation V | Preparation I, but without lipomicron of vitamin A palmitate. |

The pH of the aqueous phase was adjusted to 2.2 for all the products, except the placebo (pH=5.7). The placebo product corresponded to the preparation in Example 1 without α-hydroxy acids, without salicylic acid and without a retinoid.

Method and area of application:

Three areas of 10 cm² each were defined on the front side of each forearm. Two applications of an oil/water cream containing 10% of dihydroxyacetone were carried out at an interval of 24 hours to obtain a clear and uniform coloration. A defined quantity (0.02 ml, that being 2 mg/cm$^2$) of the six products was applied evenly as a thin layer using a fingerstall with massaging for a few seconds, over 9 days, at a rate of two applications/day. The products were applied with a 1 ml Terumo Ribbon Pack syringe.

Measurements:

The measurements were taken at the following times:

T0=before application of DHA,

T1=48 hours after two applications of DHA,

T2, T3, T4, T5, T6, T7, T8=after 1, 2, 3, 4, 7, 8 and 9 days of applications of the products being studied.

Technical procedure:

The determination of the color of the skin was made using a chromameter (for example CR-200 MINOLTA Chromameter) equipped with a pulsed xenon arc lamp. The principle of the apparatus was based on the measurement of the light reflected by the cutaneous surface. The cells of the chromameter convert the light received into a current whose intensity was proportional to the brightness of the light. The current was then converted into a digital signal itself processed by a microprocessor which determined the tristimulus values of the surface in the area of color selected (here area L* a* b*) (see Minolta "Analysis of colors—control of colors: from perception to instrumentation" January 1989). The color as perceived had three dimensions: shade, saturation and brightness. The chromaticity included the shade and the saturation; it was specified by 2 chromaticity coordinates a* and b*. Each value corresponded to the average of the 3 measurements.

B) Results

They were recorded on observation sheets, one per participant. The parameter studied during the study was the yellow component b*. This parameter had been chosen because of its linear decrease over time, directly linked to a loss in intensity of the coloration obtained after application of self-tanning cream (see Pierard and Pierard—Franchimont, Dermatology, 1992, 663/348).

The calculation of the percentage reduction of parameter b* relative to T1 was made according to the following formula:

$$\% \ Tx = (T1 - Tx)/(T1 - T0) \times 100$$

where Tx represented consecutively T2, T3, T4, T5, T6, T7 and T8. The average values (for 5 subjects) were set out in the following table:

| % dim. b*/ time | Prep. I | Prep. II | Prep. III | Prep. IV | Prep. V |
|---|---|---|---|---|---|
| % T2 | 11 | 4 | 6 | 10 | 12 |
| % T3 | 18 | 11 | 14 | 16 | 17 |
| % T4 | 26 | 15 | 18 | 21 | 23 |

-continued

| % dim. b*/ time | Prep. I | Prep. II | Prep. III | Prep. IV | Prep. V |
|---|---|---|---|---|---|
| % T5 | 34 | 22 | 25 | 25 | 32 |
| % T6 | 60 | 31 | 43 | 38 | 45 |
| % T7 | 71 | 36 | 61 | 44 | 59 |
| % T8 | 81 | 52 | 74 | 59 | 75 |

Analysis of the results

After application of the cream containing 10% DHA (T1), an increase in the values of parameter b* relative to the start (T0) was recorded. Then, the values of b* followed a progressive decrease during the 9 days of application for all the products tested. This decrease was expressed as a percentage relative to T1 and it was greater for preparation I (complete product) relative to the other preparations (II, III, IV and V) containing the mixture of 2 of the active ingredients only. The advantage of the preparation of the invention became greater after several weeks of application. Moreover, the product was quite harmless.

Various modifications of the compositions and method of the invention may be made without departing from the spirit or scope thereof and it is to be understood that the invention is intended to be limited only as defined in the appended claims.

What we claim is:

1. A cosmetic or dermatological composition containing a skin enhancing agent consisting essentially of a) at least one α-hydroxy acid, b) salicylic acid or esters thereof and c) 0.02 to 2.0%, of vitamin A palmitate.

2. A composition of claim 1 where component b) is salicylic acid.

3. A composition of claim 1 containing 3 to 20% by weight of a), 0.1 to 5% of salicylic acid or 0.2 to 10% by weight of esters of salicylic acid in b) and 0.02 to 2% of c), all % by weight based on the total composition.

4. A composition of claim 1 also containing nordihydroreguaiaretic acid or esters thereof.

5. A composition of claim 1 consisting essentially of a) 4 to 15% by weight of lactic acid, b) 0.3 to 4% by weight of salicylic acid or 0.6 to 8% by weight of at least one ester of salicylic acid and c) 0.04 to 1% by weight of vitamin A palmitate.

6. A method of enhancing the skin of a warm-blooded animal comprising applying a skin enhancing amount of a composition of claim 1 to the skin of a warm-blooded animal.

7. The method of claim 6 wherein the composition contains 3 to 20% by weight of a), 0.1 to 5% of salicylic acid or 0.2 to 10% by weight of esters of salicylic acid in b) and 0.02 to 2% of c), all % by weight based on the total composition.

* * * * *